United States Patent
Old et al.

(10) Patent No.: US 6,812,240 B1
(45) Date of Patent: Nov. 2, 2004

(54) 8-AZAPROSTAGLANDIN CARBONATE AND THIOCARBONATE ANALOGS AS THERAPEUTIC AGENTS

(75) Inventors: David W. Old, Irvine, CA (US); Thang D. Dinh, Garden Grove, CA (US); Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/765,418

(22) Filed: Jan. 26, 2004

Related U.S. Application Data

(62) Division of application No. 10/453,818, filed on Jun. 2, 2003, now Pat. No. 6,734,201.

(51) Int. Cl.[7] .................. A61K 31/41; C07D 257/04; C07D 207/18
(52) U.S. Cl. .................. 514/381; 548/253; 548/413; 548/518; 548/543; 548/551; 514/422; 514/424
(58) Field of Search .................. 548/253, 413, 548/518, 543, 551; 514/381, 422, 424

(56) References Cited

U.S. PATENT DOCUMENTS

| | | | |
|---|---|---|---|
| 4,994,274 A | 2/1991 | Chan et al. | |
| 5,028,624 A | 7/1991 | Chan et al. | |
| 5,034,413 A | 7/1991 | Chan et al. | |
| 5,446,041 A | 8/1995 | Chan et al. | |
| 6,573,294 B1 * | 6/2003 | Old et al. | 514/424 |
| 6,734,201 B1 * | 5/2004 | Old et al. | 514/381 |
| 6,734,206 B1 * | 5/2004 | Old et al. | 514/424 |

FOREIGN PATENT DOCUMENTS

| | | |
|---|---|---|
| EP | 1 121 939 A2 | 8/2001 |
| JP | 2001-233792 | 8/2001 |
| WO | WO01/46140 A1 | 6/2001 |
| WO | WO 02/24647 A1 | 3/2002 |
| WO | WO 02/042268 A2 | 5/2002 |
| WO | WO 03/007941 A1 | 1/2003 |
| WO | 03/009872 A1 | 6/2003 |

OTHER PUBLICATIONS

Bito, L.Z., *Biological Protection with Prostaglandins*, Cohen, M.M., ed., Boca Raton, Fla, CRC Press Inc., 1985, pp. 231–252.

Bito, L.Z., *Applied Pharmacology in the Medical Treatment of Glaucomas*, Drance, S.M. and Neufeld, A.H. eds, New York, Grune & Stratton, 1984, pp. 477–505.

Nilsson et al, Invest. *Ophthalmol. Vis. Sci.* (suppl), 284 (1987).

Bito, L.Z., *Arch. Ophthalmol.* 105, 1036 (1987).

Siebold et al, *Prodrug* 5 3 1989.

* cited by examiner

*Primary Examiner*—Golam M M Shameem
(74) *Attorney, Agent, or Firm*—Robert J. Baran; Martin A. Voet; Carlos A. Fisher

(57) ABSTRACT

The present invention provides a compound represented by the general formula I;

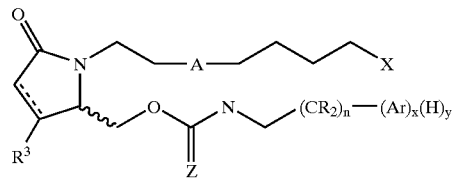

Figure 1:
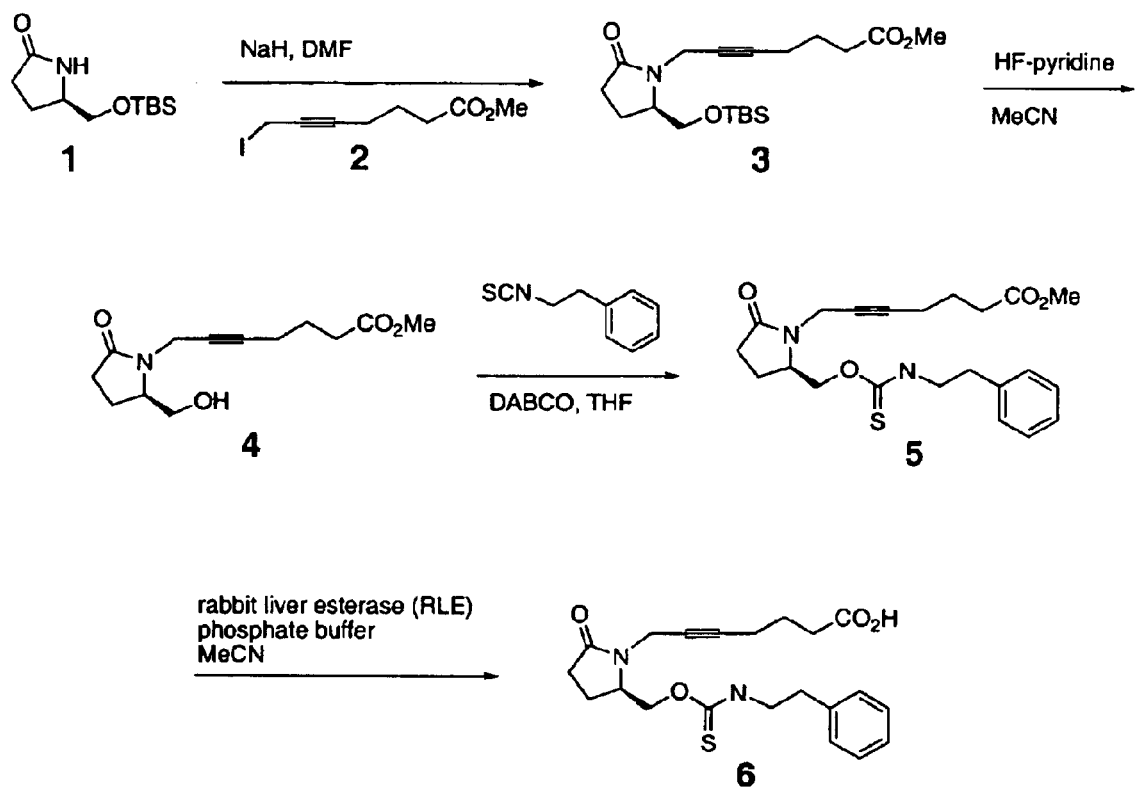

wherein A, Ar, X, Z, n, x, y, R and $R^3$ are as defined in the specification.

1 Claim, 5 Drawing Sheets

8-AZAPROSTAGLANDIN CARBONATE AND THIOCARBONATE ANALOGS AS THERAPEUTIC AGENTS

RELATED APPLICATION

This patent application is a divisional of application Ser. No. 10/453,818 now U.S. Pat. No. 6,734,201 filed Jun. 2, 2003 which is hereby incorporated by reference herein.

BACKGROUND OF THE INVENTION

1. Field of the Invention

The present invention relates to 8-Azaprostaglandin carbonate and thiocarbonate analogues as therapeutic agents, e.g. for the management of glaucoma.

2. Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical b-adrenoreceptor antagonists have traditionally been the drugs of choice for treating glaucoma.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the following structural formula:

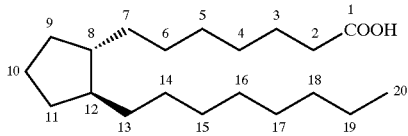

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known experimental results indicate that the prostaglandin-induced reduction in intraocular pressure results from increased uveoscleral outflow [Nilsson et.al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalinol.* 105. 1036 (1987), and Siebold et.al., Prodrug 5 3 (1989)].

Whereas prostaglandins appear to be devoid of significant intraocular side effects, ocular surface (conjunctival) hyperemia and foreign-body sensation have been consistently associated with the topical ocular use of such compounds, in particular PGF2α and its prodrugs, e.g., its 1-isopropyl ester, in humans. The clinical potentials of prostaglandins in the management of conditions associated with increased ocular pressure, e.g. glaucoma are greatly limited by these side effects.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 (filed 10 Oct. 1990, now U.S. Pat. No. 5,446,041), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 175, 476 (filed 29 Dec. 1993). Similarly, 11,15- 9,15 and 9,11-diesters of prostaglandins, for example 11,15-pivaloyl $PGF_{2\alpha}$ are known to have ocular hypotensive activity. See the co-pending patent applications U.S. Ser. No. 385,645 (filed 7 Jul. 1989, now U.S. Pat. No. 4,994,274), Ser. No.

584,370 (filed 18 Sep. 1990, now U.S. Pat. No. 5,028,624) and Ser. No. 585,284 (filed 18 Sep. 1990, now U.S. Pat. No. 5,034,413). The disclosures of all of these patent applications are hereby expressly incorporated by reference.

8-Azaprostaglandin analogs are disclosed in PCT Patent Applications WO 01/46140 A1, WO 02/042268 A2, WO 02/24647 A1, WO 03/007941 A1, EP 1 121 939 A2 and Japanese Patent 2001-233792.

SUMMARY OF THE INVENTION

The present invention provides therapeutic agents comprising a compound of formula I

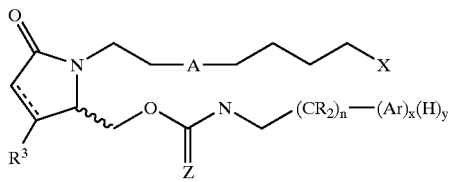

wherein a wavy line represents either the α configuration or the β configuration and a dotted line represents the presence or absence of a double bond;

A represents a single bond or a cis double (alkene) bond or a triple (alkyne) bond;

X is $CO_2R$, $CONR_2$, $CH_2OR$, $P(O)(OR)_2$, $CONRSO_2R$, $SONR_2$ or

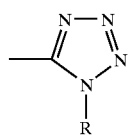

n is 0 or an integer of from 1 to 4;

x and y are 0 or 1, provided however when x is 1, y is 0 and when x is 0, y is 1;

Z is S or O;

R is H or $R^1$;

$R^1$ is $C_1$–$C_5$ lower alkyl or alkenyl;

Ar is selected from the group consisting of aryl or heteroaryl radicals, having from 4 to 10 carbon atoms, e.g. phenyl, thienyl, furanyl, pyridyl, benzothienyl, benzofuranyl, naphthyl, or substituted derivatives of said aryl or heteroaryl radicals, wherein the substituents maybe selected from the group consisting of $C_1$–$C_5$ alkyl, halogen, $CF_3$, CN, $NO_2$, $NR_2$, $CO_2R$ and OR and $R^3$ is R, OR, $CH_2OR$ or COR.

These compounds are useful for treating diseases and conditions which are responsive to treatment with prostaglandin analogues, e.g. glaucoma; cardiovascular; e.g. acute myocardial infarction, vascular thrombosis, hypertension, pulmonary hypertension, ischemic heart disease, congestive heart failure, and angina pectoris; pulmonary-respiratory; gastrointestinal; reproductive and allergic diseases; osteoporosis and shock.

In a further aspect, the present invention relates to an ophthalmic solution comprising a therapeutically effective amount of a compound of formula (I), wherein the symbols have the above meanings, or a pharmaceutically acceptable salt thereof, in admixture with a non-toxic, ophthalmically acceptable liquid vehicle, packaged in a container suitable for metered application.

In a still further aspect, the present invention relates to a pharmaceutical product, comprising a container adapted to dispense its contents in a metered form; and an ophthalmic solution therein, as hereinabove defined.

DESCRIPTION OF THE DRAWING FIGURE

Figure 2:
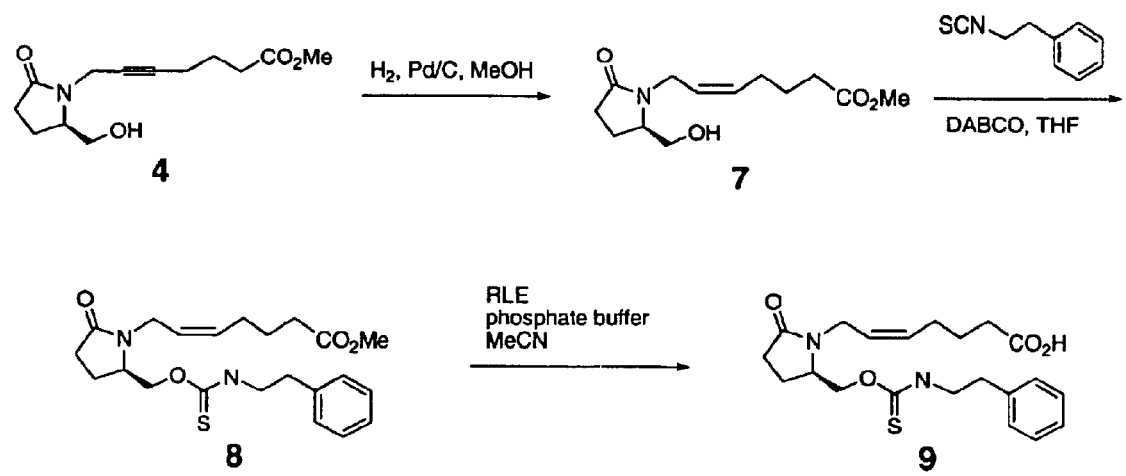
Figure 3:
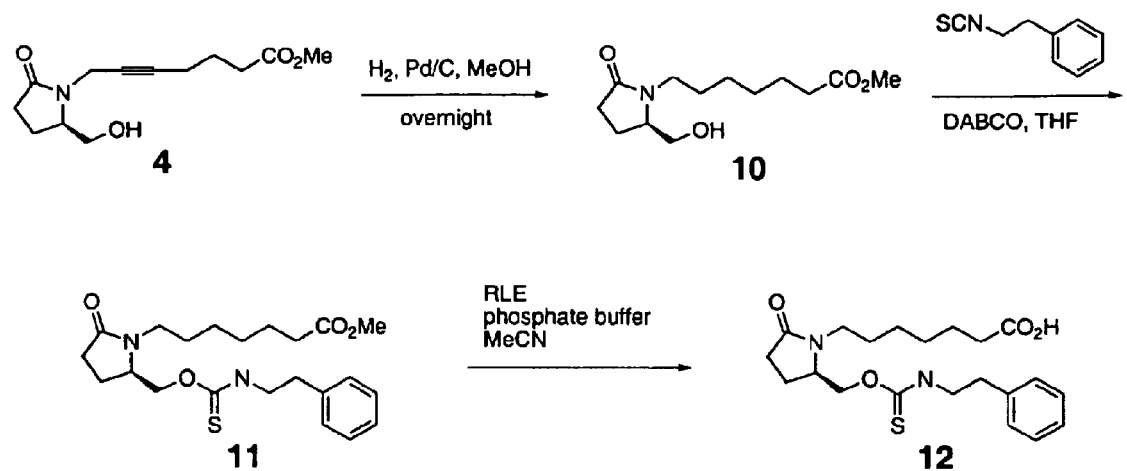
Figure 4:
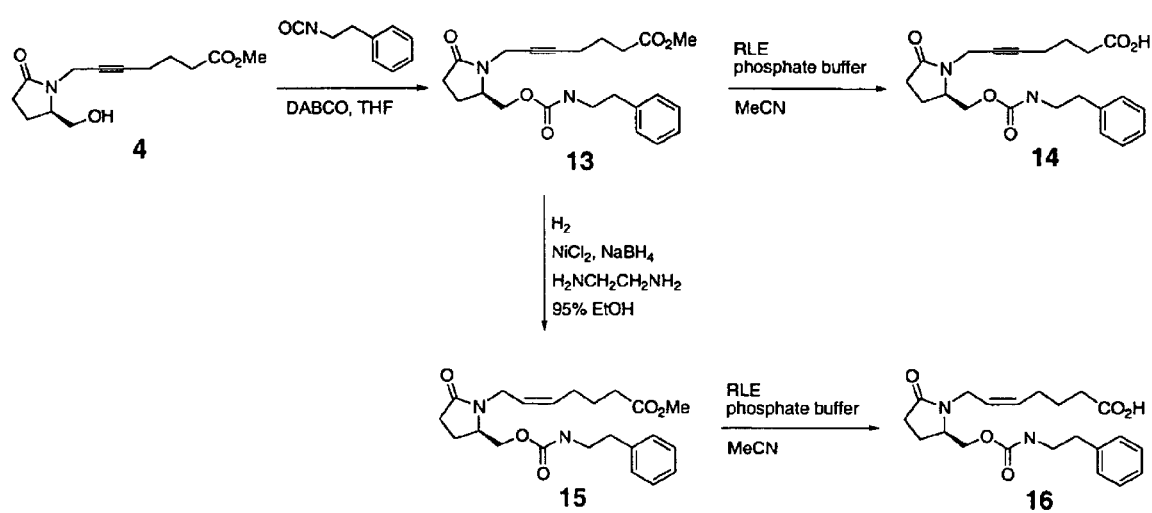
Figure 5:
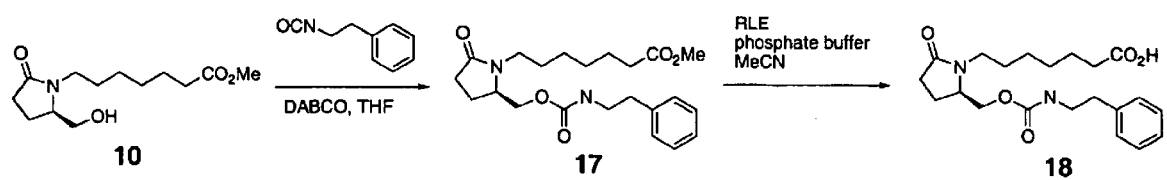

FIGS. 1–5 show schematics for the preparation of the compounds of the invention wherein the numbered compounds and intermediates correspond to the numbered compounds and intermediates of the Examples.

DETAILED DESCRIPTION OF THE INVENTION

The present invention relates to 8-Azaprostaglandin analogs which are useful as ocular hypotensives or for treating other diseases and conditions which are responsive to treatment with prostaglandin analogues. The compounds used in

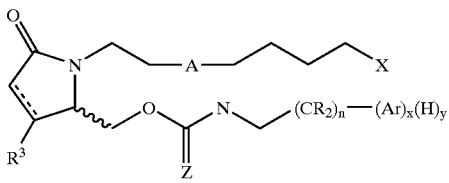

accordance with the present invention are encompassed by the following structural formula I:

The preferred group of the compounds of the present invention includes compounds that have the following structural formula II.

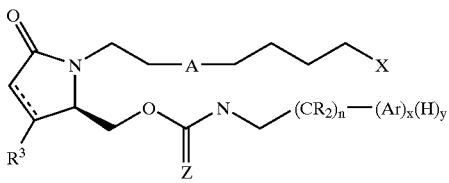

wherein a triangle at position C-12 represents β orientation.

The more preferred group of compounds have the following structural formula III

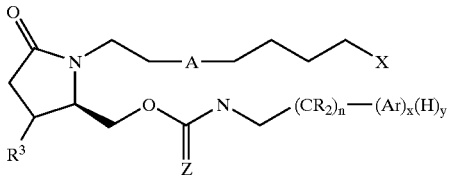

In the above formulae, the substituents and symbols are as hereinabove defined.

In the above formulae:

Preferably X is $CO_2R$ and more preferably R is H or $CH_3$

Preferably n is 0 or 1 and Ar is phenyl or n is 3 and x is 0

Preferably $R^3$ is H

The above compounds of the present invention may be prepared by methods that are known in the art or according to the working examples below. The compounds, below, are especially preferred representative, of the compounds of the present invention.

7-((R)-2-Oxo-5-phenethylthiocarbamoyloxymethyl-pyrrolidin-1-yl)-hept-5-ynoic acid methyl ester
7-((R)-2-Oxo-5-phenethylthiocarbamoyloxymethyl-pyrrolidin-1-yl)-hept-5-ynoic acid
(Z)-7-((R)-2-Oxo-5-phenethylthiocarbamoyloxymethyl-pyrrolidin-1-yl)-hept-5-enoic acid methyl ester
(Z)-7-((R)-2-Oxo-5-phenethylthiocarbamoyloxymethyl-pyrrolidin-1-yl)-hept-5-enoic acid
7-((R)-2-Oxo-5-phenethylthiocarbamoyloxymethyl-pyrrolidin-1-yl)-heptanoic acid methyl ester
7-((R)-2-Oxo-5-phenethylthiocarbamoyloxymethyl-pyrrolidin-1-yl)-heptanoic acid
7-((R)-2-Oxo-5-phenethylcarbamoyloxymethyl-pyrrolidin-1-yl)-hept-5-ynoic acid methyl ester
7-((R)-2-Oxo-5-phenethylcarbamoyloxymethyl-pyrrolidin-1-yl)-hept-5-ynoic acid
(Z)-7-((R)-2-Oxo-5-phenethylcarbamoyloxymethyl-pyrrolidin-1-yl)-hept-5-enoic acid methyl ester
(Z)-7-((R)-2-Oxo-5-phenethylcarbamoyloxymethyl-pyrrolidin-1-yl)-hept-5-enoic acid
7-((R)-2-Oxo-5-phenethylcarbamoyloxymethyl-pyrrolidin-1-yl)-heptanoic acid methyl ester
7-((R)-2-Oxo-5-phenethylcarbamoyloxymethyl-pyrrolidin-1-yl)-heptanoic acid
7-((R)-2-Benzylcarbamoyloxymethyl-5-oxo-pyrrolidin-1-yl)-hept-5-ynoic acid methyl ester
7-((R)-2-Benzylcarbamoyloxymethyl-5-oxo-pyrrolidin-1-yl)-hept-5-ynoic acid
(Z)-7-((R)-2-Benzylcarbamoyloxymethyl-5-oxo-pyrrolidin-1-yl)-hept-5-enoic acid methyl ester
(Z)-7-((R)-2-Benzylcarbamoyloxymethyl-5-oxo-pyrrolidin-1-yl)-hept-5-enoic acid
7-((R)-2-Benzylcarbamoyloxymethyl-5-oxo-pyrrolidin-1-yl)-heptanoic acid methyl ester
7-((R)-2-Benzylcarbamoyloxymethyl-5-oxo-pyrrolidin-1-yl)-heptanoic acid
7-((R)-2-Oxo-5-pentylcarbamoyloxymethyl-pyrrolidin-1-yl)-hept-5-ynoic acid methyl ester
7-((R)-2-Oxo-5-pentylcarbamoyloxymethyl-pyrrolidin-1-yl)-hept-5-ynoic acid
(Z)-7-((R)-2-Oxo-5-pentylcarbamoyloxymethyl-pyrrolidin-1-yl)-hept-5-enoic acid methyl ester
(Z)-7-((R)-2-Oxo-5-pentylcarbamoyloxymethyl-pyrrolidin-1-yl)-hept-5-enoic acid
7-((R)-2-Oxo-5-pentylcarbamoyloxymethyl-pyrrolidin-1-yl)-heptanoic acid methyl ester
7-((R)-2-Oxo-5-pentylcarbamoyloxymethyl-pyrrolidin-1-yl)-heptanoic acid Pharmaceutical compositions including said compounds may be prepared by combining a therapeutically effective amount of at least one compound according to the present invention, or a pharmaceutically acceptable acid addition salt thereof, as an active ingredient, with conventional ophthalmically acceptable pharmaceutical excipients, and by preparation of unit dosage forms. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 6.5 and 7.2 with an appropriate buffer system. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

This invention is further illustrated by the following non-limiting Examples.

EXAMPLE 1

7-((R)-2-Oxo-5-phenethylthiocarbamoyloxymethyl-pyrrolidin-1-yl)-hept-5-ynoic acid methyl ester (5)

Step 1. Alkylation of Amide 1 to Give 3

Sodium hydride (60% dispersion in oil, 233 mg, 5.81 mmol) was added to a solution of amide 1 (1.33 g, 5.81 mmol) in DMF (10 mL). The reaction mixture was stirred at rt for 1 h, then iodide 2 (1.54 g, 5.81 mmol) was added as a solution in DMF (3 mL) via cannula. The reaction was heated at 90° C. for 21 h then cooled to rt. Aqueous HCl (1.0 M, 50 mL) was added and the mixture was extracted with EtOAc (3×75 mL). The combined organic phase was washed with brine (3×50 mL), dried ($Na_2SO_4$), filtered and concentrated in vacuo. Purification of the residue by flash column chromatography on silica (100% $CH_2Cl_2 \rightarrow 1\%$ $MeOH/CH_2Cl_2$, gradient) afforded 910 mg (43%) of 3.

Step 2. Deprotection of 3 to Give 4

HF-pyridine (4.0 mL) was added to a solution of silyl ether 3 (857 mg, 2.33 mmol) in MeCN (8.0 mL) in a plastic scintillation vial. After 5 h at rt, the reaction was quenched with saturated aqueous $NaHCO_3$ (50 mL) and the mixture was extracted with EtOAc (3×50 mL). The combined organic phase was washed with brine (50 mL), dried ($Na_2SO_4$), filtered and concentrated in vacuo. Purification of the residue by flash column chromatography on silica (100% $CH_2Cl_2 \rightarrow 2\%$ $MeOH/CH_2Cl_2$, gradient) afforded 570 mg (97%) of 4. Step 3. Thiocarbamoylation of 4 to give 5

Phenethyl isothiocyanate (70 µL, 0.47 mmol) and DABCO (66 mg, 0.59 mmol) were added to a solution of alcohol 4 (99 mg, 0.39 mmol) in THF (1.5 mL). The reaction was heated at reflux for 6 h, then cooled to rt and concentrated in vacuo. Purification of the residue by flash column chromatography on silica (100% $CH_2Cl_2 \rightarrow 20\%$ EtOAc/$CH_2Cl_2 \rightarrow 2\%$ $MeOH/CH_2Cl_2$) afforded 22 mg (14%) of the title compound (5).

EXAMPLE 2

7-((R)-2-Oxo-5-phenethylthiocarbamoyloxymethyl-pyrrolidin-1-yl)-hept-5-ynoic acid (6)

Rabbit liver esterase (134 units/mg, 1 mg), ester 5 (6.0 mg, 0.015 mmol), MeCN (0.1 mL) and pH 7.2 phosphate buffer (2.0 mL) were stirred together at rt overnight. MeCN (5.0 mL) was added and the reaction was concentrated in vacuo. Purification of the residue by flash column chromatography on silica (100% $CH_2Cl_2 \rightarrow 2\%$ $MeOH/CH_2Cl_2$, gradient) afforded 3.2 mg (55%) of the title compound (6).

EXAMPLE 3

(Z)-7-((R)-2-Oxo-5-phenethylthiocarbamoyloxymethyl-pyrrolidin-1-yl)-hept-5-enoic acid methyl ester (8)

Step 1. Reduction of 4 to Give 7

Palladium on carbon (10 mol%, 5 mg) was added to a solution of alkyne 4 (27 mg, 0.11 mmol) in MeOH (1.5 mL). The flask was evacuated and refilled with hydrogen (3×), and the reaction mixture was stirred vigorously under a balloon of hydrogen for 1.3 h. The mixture was then filtered through celite, washing with MeOH (5 mL) and the filtrate was concentrated in vacuo to afford 26 mg (95%) of alkene 7.

Step 2. Thiocarbamoylation of 7 to Give 8

In accordance with Example 1, step 3, 7 (26 mg, 0.10 mmol) was converted into 35 mg (83%) of the title compound (8) after chromatography (100% $CH_2Cl_2 \rightarrow 60\%$ $EtOAc/CH_2Cl_2$, gradient).

EXAMPLE 4

(Z)-7-((R)-2-Oxo-5-phenethylthiocarbamoyloxymethyl-pyrrolidin-1-yl)-hept-5-enoic acid (9)

In accordance with Example 2, 8 (11 mg, 0.026 mmol) was converted into 7.4 mg (70%) of the title compound (9).

EXAMPLE 5

7-(R)-2-Oxo-5-phenethylthiocarbamoyloxymethyl-pyrrolidin-1-yl)-heptanoic acid methyl ester (11)

Step 1. Reduction of 4 to Give 10

Palladium on carbon (10 mol %, 10 mg) was added to a solution of alkyne 4 (47 mg, 0.19 mmol) in MeOH (1.5 mL).

The flask was evacuated and refilled with hydrogen (3×), and the reaction mixture was stirred vigorously under a balloon of hydrogen for 21 h. The mixture was then filtered through celite, washing with MeOH (5 mL) and the filtrate was concentrated in vacuo to afford 42 mg (88%) of alkane 10.

Step 2. Thiocarbamoylation of 10 to Give 11

In accordance with Example 1, step 3, 10 (19 mg, 0.074 mmol) was converted into 28 mg (90%) of the title compound (11) after chromatography (100% $CH_2Cl_2 \rightarrow 50\%$ $EtOAc/CH_2Cl_2$, gradient).

EXAMPLE 6

7-((R)-2-Oxo-5-phenethylthiocarbamoyloxymethyl-pyrrolidin-1-yl)-heptanoic acid (12)

In accordance with Example 2, 11 (17 mg, 0.040 mmol) was converted into 11 mg (67%) of the title compound (12).

EXAMPLE 7

7-((R)-2-Oxo-5-phenethylcarbamoyloxymethyl-pyrrolidin-1-yl)-hept-5-ynoic acid methyl ester (13)

A solution of 4 (52 mg, 0.21 mmol), DABCO (35 mg, 0.32 mmol) and phenethyl isocyanate (60 µL, 0.43 mmol) in THF (1.5 mL) was heated at reflux for 22.5 h. The reaction was cooled to rt then concentrated in vacuo. Purification of the residue by flash column chromatography (100% $CH_2Cl_2 \rightarrow 50\%$ $EtOAc/CH_2Cl_2$, gradient) afforded 86 mg (quant.) of the title compound (13).

EXAMPLE 8

7-((R)-2-Oxo-5-phenethylcarbamoyloxymethyl-pyrrolidin-1-yl)-hept-5-ynoic acid (14)

In accordance with Example 2, 13 (16 mg, 0.040 mmol) was converted into 11 mg (72%) of the title compound (14).

EXAMPLE 9

(Z)-7-((R)-2-Oxo-5-phenethylcarbamoyloxymethyl-pyrrolidin-1-yl)-hept-5-enoic acid methyl ester (15)

95% Ethanol (1.0 mL) was added to a slowly stirred mixture of nickel (II) chloride (86 mg, 0.66 mmol) and sodium borohydride (12 mg, 0.33 mmol) under nitrogen. The mixture immediately turned black. After 15 min, ethylenediamine (70 µL, 1.04 mmol) was added. After an additional 15 min, a solution of alkyne 13 (53 mg, 0.13 mmol) in 95% ethanol (1.0 mL) was added. The flask was evacuated and refilled with hydrogen (3×), and the reaction mixture was stirred vigorously under a balloon of hydrogen for 22 h. The mixture was then filtered through celite, washing with MeOH (5 mL) and the filtrate was concentrated in vacuo. Purification of the residue by flash column chromatography on silica (100% $CH_2Cl_2 \rightarrow 50\%$ $EtOAc/CH_2Cl_2$, gradient) afforded 30 mg (56%) of the title compound (15).

EXAMPLE 10

(Z)-7-((R)-2-Oxo-5-phenethylcarbamoyloxymethyl-pyrrolidin-1-yl)-hept-5-enoic acid (16)

In accordance with Example 2, 15 (17 mg, 0.042 mmol) was converted into 12 mg (73%) of the title compound (16).

EXAMPLE 11

7-((R)-2-Oxo-5-phenethylcarbamoyloxymethyl-pyrrolidin-1-yl)-heptanoic acid methyl ester (17)

A solution of 10 (22 mg, 0.085 mmol), DABCO (14 mg, 0.13 mmol) and phenethyl isocyanate (14 µL, 0.10 mmol) in THF (1.0 mL) was heated at reflux for 22.5 h. The reaction was cooled to rt then concentrated in vacuo. Purification of the residue by flash column chromatography (100%

CH$_2$Cl$_2$→50% EtOAc/CH$_2$Cl$_2$, gradient) afforded 34 mg (98%) of the title compound (17).

EXAMPLE 12
7-((R)-2-Oxo-5-phenethylcarbamoyloxymethyl-pyrrolidin-1-yl)-heptanoic acid (18)

In accordance with Example 2, 17 (17 mg, 0.042 mmol) was converted into 8 mg (48%) of the title compound (18).

EXAMPLE 13
7-((R)-2-Benzylcarbamoyloxymethyl-5-oxo-pyrrolidin-1-yl)-hept-5-ynoic acid methyl ester (19)

DABCO (51 mg, 0.45 mmol) and benzyl isocyanate (45 µL, 0.36 mmol) were added to a solution of 4 (76 mg, 0.30 mmol) in THF (2.0 mL). The reaction was heated at reflux overnight. After 18 h, the reaction was cooled to rt and concentrated in vacuo. Purification of the residue by flash column chromatography (2 times: 1$^{st}$ 100% CH$_2$Cl$_2$→2% MeOH/CH$_2$Cl$_2$, gradient and then 2$^{nd}$ 10% EtOAc/CH$_2$Cl$_2$→50% EtOAc/CH$_2$Cl$_2$, gradient) afforded 105 mg (91%) of the title compound (19).

EXAMPLE 14
7-((R)-2-Benzylcarbamoyloxymethyl-5-oxo-pyrrolidin-1-yl)-hept-5-ynoic acid (20)

In accordance with Example 2, 19 (14 mg, 0.036 mmol) was converted into 2 mg (15%) of the title compound (20) after chromatography (100% CH$_2$Cl$_2$→40% EtOAc/CH$_2$Cl$_2$→2% MeOH/CH$_2$Cl$_2$, gradient).

EXAMPLE 15
(Z)-7-((R)-2-Benzylcarbamoyloxymethyl-5-oxo-pyrrolidin-1-yl)-hept-5-enoic acid methyl ester (21)

In accordance with Example 9, 19 (82 mg, 0.21 mmol) was converted into 71 mg (86%) of the title compound (21) after chromatography (10%→50% EtOAc/CH$_2$Cl$_2$).

EXAMPLE 16
(Z)-7-((R)-2-Benzylcarbamoyloxymethyl-5-oxo-pyrrolidin-1-yl)-hept-5-enoic acid (22)

In accordance with Example 2, 21 (18 mg, 0.046 mmol) was converted into 17 mg (98%) of the title compound (22).

EXAMPLE 17
7-((R)-2-Benzylcarbamoyloxymethyl-5-oxo-pyrrolidin-1-yl)-heptanoic acid methyl ester (23)

Palladium on carbon (10 mol %, 7 mg) was added to a solution of alkene 21 (39 mg, 0.10 mmol) in MeOH (2.5 mL). The flask was evacuated and refilled with hydrogen (3×), and the reaction mixture was stirred vigorously under a balloon of hydrogen for 3.5 h. The mixture was then filtered through celite, washing with MeOH (5 mL) and the filtrate was concentrated in vacuo to afford 33 mg (85%) of the title compound (23).

EXAMPLE 18
7-((R)-2-Benzylcarbamoyloxymethyl-5-oxo-pyrrolidin-1-yl)-heptanoic acid (24)

In accordance with Example 2, 23 (19 mg, 0.049 mmol) was converted into 18 mg (98%) of the title compound (24).

EXAMPLE 19
7-((R)-2-Oxo-5-pentylcarbamoyloxymethyl-pyrrolidin-1-yl)-hept-5-ynoic acid methyl ester (25)

DABCO (41 mg, 0.36 mmol) and pentyl isocyanate (37 µL, 0.28 mmol) were added to a solution of 4 (60 mg, 0.24 mmol) in THF (2.0 mL). The reaction was heated at reflux overnight. After 21 h, the reaction was cooled to rt and concentrated in vacuo. Purification of the residue by flash column chromatography (100% CH$_2$Cl$_2$→50% EtOAc/CH$_2$Cl$_2$, gradient) afforded 82 mg (94%) of the title compound (25).

EXAMPLE 20
7-((R)-2-Oxo-5-pentylcarbamoyloxymethyl-pyrrolidin-1-yl)-hept-5-ynoic acid (26)

In accordance with Example 2, 25 (9 mg, 0.025 mmol) was converted into 5 mg (58%) of the title compound (26).

EXAMPLE 21
(Z)-7-((R)-2-Oxo-5-pentylcarbamoyloxymethyl-pyrrolidin-1-yl)-hept-5-enoic acid methyl ester (27)

In accordance with Example 9, 25 (54 mg, 0.15 mmol) was converted into 48 mg (88%) of the title compound (27).

EXAMPLE 22
(Z)-7-((R)-2-Oxo-5-pentylcarbamoyloxymethyl-pyrrolidin-1-yl)-hept-5-enoic acid (28)

In accordance with Example 2, 27 (16 mg, 0.043 mmol) was converted into 15 mg (98%) of the title compound (28).

EXAMPLE 23
7-(R)-2-Oxo-5-pentylcarbamoyloxymethyl-pyrrolidin-1-yl)-heptanoic acid methyl ester (29)

Palladium on carbon (10 mol %, 5 mg) was added to a solution of alkene 27 (24 mg, 0.065 mmol) in MeOH (2.0 mL). The flask was evacuated and refilled with hydrogen (3×), and the reaction mixture was stirred vigorously under a balloon of hydrogen for 5 h. The mixture was then filtered through celite, washing with MeOH (5 mL) and the filtrate was concentrated in vacuo to afford 24 mg (99%) of the title compound (29).

EXAMPLE 24
7-((R)-2-Oxo-5-pentylcarbamoyloxymethyl-pyrrolidin-1-yl)-heptanoic acid (30)

In accordance with Example 2, 29 (17 mg, 0.046 mmol) was converted into 8 mg (49%) of the title compound (30).

The compounds of this invention are useful in lowering elevated intraocular pressure in mammals, e.g. humans, and for treating other diseases and conditions which are responsive to treatment with prostaglandin analogues, e.g. glaucoma; cardiovascular; e.g. acute myocardial infarction, vascular thrombosis, hypertension, pulmonary hypertension, ischemic heart disease, congestive heart failure, and angina pectoris; pulmonary-respiratory; gastrointestinal; reproductive and allergic diseases; osteoporosis and shock.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A method of treating ocular hypertension or glaucoma which comprises administering to an animal having ocular hypertension or glaucoma a therapeutically effective amount of a compound represented by the general formula I;

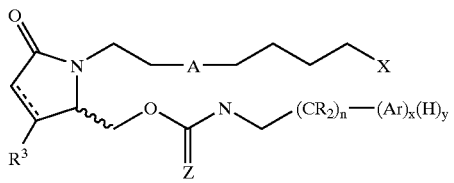

wherein a wavy line represents either the α configuration or the β configuration and a dotted line represents the presence or absence of a double bond;

A represents a single bond or a cis double (alkene) bond or a triple (alkyne) bond;

X is $CO_2R$, $CONR_2$, $CH_2OR$, $P(O)(OR)_2$, $CONRSO_2R$, $SONR_2$ or

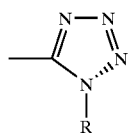

n is 0 or an integer of from 1 to 4;

x and y are 0 or 1, provided however when x is 1, y is 0 and when x is 0, y is 1;

Z is S or O;

R is H or $R^2$;

$R^1$ is H, $R^2$, phenyl, or $COR^2$;

$R^2$ is $C_1$–$C_5$ lower alkyl or alkenyl;

Ar is selected from the group consisting of aryl or heteroaryl radicals, having from 4 to 10 carbon atoms, or substituted derivatives of said aryl or heteroaryl radicals, wherein the substituents maybe selected from the group consisting of $C_1$–$C_5$ alkyl, halogen, $CF_3$, CN, $NO_2$, $NR_2$, $CO_2R$ and OR and $R_3$ is R, OR, $CH_2OR$ or COR.

* * * * *

UNITED STATES PATENT AND TRADEMARK OFFICE
CERTIFICATE OF CORRECTION

PATENT NO. : 6,812,240 B1
DATED : November 2, 2004
INVENTOR(S) : Old et al.

It is certified that error appears in the above-identified patent and that said Letters Patent is hereby corrected as shown below:

Column 2,
Line 36, delete "Ophthalinol." and insert in place thereof -- Ophthalmol. --
Line 49, delete "PGFs2α" and insert in place thereof -- $PGF_{2\alpha}$ --

Signed and Sealed this

Thirty-first Day of May, 2005

JON W. DUDAS
*Director of the United States Patent and Trademark Office*